United States Patent [19]
Poff et al.

[11] Patent Number: 6,123,667
[45] Date of Patent: Sep. 26, 2000

[54] RETRACTING TISSUE USING PHOTOADHERING ADHESIVE

[75] Inventors: Bradley C. Poff, Chelmsford; Stephen J. Herman, Andover; Dean M. Pichon, Arlington; Amarpreet S. Sawhney, Bedford, all of Mass.

[73] Assignee: Focal, Inc., Lexington, Mass.

[21] Appl. No.: 09/045,401

[22] Filed: Mar. 20, 1998

Related U.S. Application Data

[60] Provisional application No. 60/042,054, Mar. 20, 1997.

[51] Int. Cl.$^7$ ................................................ A61B 17/00
[52] U.S. Cl. .............................................................. 600/201
[58] Field of Search ................................... 600/201, 204, 600/206, 235, 210

[56] References Cited

U.S. PATENT DOCUMENTS

| | | |
|---|---|---|
| 2,303,131 | 11/1942 | Morgan . |
| 3,376,869 | 4/1968 | Borvsko . |
| 3,526,228 | 9/1970 | Lyng . |
| 3,739,773 | 6/1973 | Schmitt et al. . |
| 3,766,910 | 10/1973 | Lake . |
| 4,511,478 | 4/1985 | Nowinski et al. . |
| 4,520,821 | 6/1985 | Schmidt et al. . |
| 4,585,458 | 4/1986 | Kurland . |
| 4,621,619 | 11/1986 | Sharpe . |
| 4,633,873 | 1/1987 | Dumican et al. . |
| 4,655,221 | 4/1987 | Devereux . |
| 4,696,301 | 9/1987 | Barabe . |
| 4,741,872 | 5/1988 | DeLuca et al. . |
| 4,826,945 | 5/1989 | Cohn et al. . |
| 4,838,884 | 6/1989 | Dumican et al. . |
| 4,899,762 | 2/1990 | Muller . |
| 4,938,763 | 7/1990 | Dunn et al. . |
| 5,026,389 | 6/1991 | Thieler . |
| 5,070,860 | 12/1991 | Grounauer . |
| 5,100,992 | 3/1992 | Cohn et al. . |
| 5,106,369 | 4/1992 | Christmas . |
| 5,160,745 | 11/1992 | DeLuca et al. . |
| 5,201,745 | 4/1993 | Tavot et al. . |

(List continued on next page.)

FOREIGN PATENT DOCUMENTS

| | | |
|---|---|---|
| 0 791 330 A2 | 8/1997 | European Pat. Off. . |
| 0 791 330 A3 | 8/1997 | European Pat. Off. . |
| 2223410 | 4/1990 | United Kingdom ................... 600/206 |
| WO 91/01688 | 2/1991 | WIPO . |
| WO 96/29987 | 3/1996 | WIPO . |
| WO 96/11021 | 4/1996 | WIPO . |
| WO 96/11671 | 4/1996 | WIPO . |
| WO 96/29370 | 9/1996 | WIPO . |
| WO 96/40354 | 12/1996 | WIPO . |
| WO 97/05185 | 2/1997 | WIPO . |

OTHER PUBLICATIONS

Sawhney et al., "Bioerodible Hydrogels Based on Photopolymerized Poly(ethylene glycol)–co–poly($\beta$–hydroxy acid) Diacrylate Macromers", Macromolecules, vol. 26, No. 4, 1993, pp. 581–587.

*Primary Examiner*—Jeffrey A. Smith
*Attorney, Agent, or Firm*—Wolf, Greenfield & Sacks, P.C.

[57] ABSTRACT

This invention describes methods and devices for stabilizing and retracting tissue during surgery, in particular internal tissue. Patches of material, preferably biodegradable, are adhered to tissue surfaces. By manipulation of the patches, for example directly with forceps, or via sutures attached to the patches, tissues can be retracted or otherwise manipulated with minimal trauma to the tissues. The method is especially useful in minimally-invasive surgery.

16 Claims, 2 Drawing Sheets

U.S. PATENT DOCUMENTS

| | | |
|---|---|---|
| 5,222,939 | 6/1993 | Tiefenbrun et al. . |
| 5,258,000 | 11/1993 | Gianturco . |
| 5,292,328 | 3/1994 | Hain et al. . |
| 5,385,156 | 1/1995 | Oliva . |
| 5,410,016 | 4/1995 | Hubbell et al. . |
| 5,462,990 | 10/1995 | Hubbell et al. . |
| 5,468,505 | 11/1995 | Hubbell et al. . |
| 5,527,864 | 6/1996 | Suggs et al. . |
| 5,529,914 | 6/1996 | Hubbell et al. . |
| 5,544,664 | 8/1996 | Benderev et al. . |
| 5,545,123 | 8/1996 | Ortiz et al. ............ 600/201 X |
| 5,567,440 | 10/1996 | Hubbell et al. . |
| 5,573,934 | 11/1996 | Hubbell et al. . |
| 5,575,815 | 11/1996 | Slepian et al. . |
| 5,582,188 | 12/1996 | Benderev et al. . |
| 5,612,050 | 3/1997 | Rowe et al. . |
| 5,613,939 | 3/1997 | Failla . |
| 5,618,850 | 4/1997 | Coury et al. . |
| 5,626,863 | 5/1997 | Hubbell et al. . |
| 5,643,177 | 7/1997 | Ortiz et al. . |
| 5,643,596 | 7/1997 | Pruss et al. . |
| 5,653,730 | 8/1997 | Hammerslag . |
| 5,855,619 | 1/1999 | Caplan et al. . |
| 5,860,948 | 1/1999 | Buscemi . |
| 5,921,979 | 7/1999 | Kovac et al. . |
| 5,957,939 | 9/1999 | Heaven et al. . | ns
RETRACTING TISSUE USING PHOTOADHERING ADHESIVE

RELATED APPLICATION

This non-provisional application claims the benefit under Title 35, U.S.C. §119(e) of, and is a continuation-in-part of, co-pending U.S. provisional application Ser. No. 60/042,054, filed Mar. 20, 1997, entitled "Biodegradable Tissue Retractor" by Bradley C. Poff et al., incorporated herein by reference.

FIELD OF THE INVENTION

The invention relates generally to surgical devices, and more particularly to materials and methods for retraction and stabilization of tissues, using biodegradable patches adhered to tissue in a releasable manner.

BACKGROUND OF THE INVENTION

During surgery, it is often necessary to retract tissue, especially internal tissue, to operate upon it or upon adjacent tissue. This is conventionally accomplished using forceps, or other mechanical gripping devices adapted for the purpose. Retraction or manipulation may also be accomplished by implanting a suture into the tissue, but there is a significant risk of tissue tearing even with strong, muscular tissue.

U.S. Pat. No. 4,621,619 (Sharpe) describes a plastic disposable, hand applied medical retractor for retracting flesh at the edges of an incision or aperture in the human or animal body. The retractor includes a hook for impaling flesh and a pad that has an adhesive surface that can be adhered to skin to anchor the retractor to keep flesh in a retracted position.

U.S. Pat. No. 4,899,762 (Muller) describes a combination surgical drape, dressing, and closure structure and method of use before, during, and after a surgical procedure. The dressing portion can be adhered to a patient over a surgical field and, after an incision is made, the incision can be retracted with retractors, forceps, or clamps secured to the dressing portion.

U.S. Pat. No. 5,026,389 (Thieler) describes a surgical method and apparatus for opening and closing a surgical wound. An elastic member is adhered across a patient's skin at a treatment site. An incision is made by cutting through the elastic member and through the patient's skin to permit a surgical procedure to be conducted. The incision is closed by reapproximating the patient's skin at the treatment site and by bringing the cut edges of the elastic member together and adhering a relatively inelastic sealing member over the elastic member to maintain the cut edges while the wound heals.

International Patent Publication No. WO 96/29370, published Sep. 26, 1996, describes a barrier or drug delivery system that is adherent to a tissue surface to which it is applied. Tissue can be stained with a photoinitiator, then a polymer solution or gel having added thereto a defined amount of the same or a different photoinitiator can be applied to the tissue. Exposure of light causes polymerization at the surface, providing adherence and forming a gel. The resulting polymerizable barrier materials are useful for sealing tissue surfaces and junctions against leaks of fluids. Tissue surfaces also can be adhered to each other. The adhesive qualities of the material are demonstrated in an example in which pieces of abdominal wall were excised from a euthanized rat and were clamped to a glass slide with binder clips. Polymeric material was adhered to the abdominal wall tissue. The polymer was urged away from the tissue and fractured, with portions remaining adherent to the tissue.

While the above and other disclosures describe, in some cases, useful tissue-adherent devices, there exists a need for retraction of soft internal tissues such as liver and spleen. Accordingly, it is an object of the present invention to provide a device for retraction of tissue, internally of a patient, in connection with a surgical procedure.

SUMMARY OF THE INVENTION

A novel technique to accomplish retraction of tissue is described herein. The present invention provides a variety of methods, kits, systems, devices, and new uses, all concerning retraction of tissue using an agent that adheres to the tissue. All of the devices, kits, and systems can be used in conjunction with improved uses and methods of the invention, and vice versa.

In one aspect, the invention provides a method that involves applying a tissue-affixing article to a surface of tissue internally of a patient. The tissue-affixing article is adhered to the surface of the tissue, and the tissue is retracted by exerting a manipulative force on the tissue-affixing article. In one embodiment the method is to affix an adhesive to tissue, internally of a patient, and to retract the tissue via the adhesive, that is, to physically manipulate the tissue by applying force directly or, preferably, indirectly, to the adhesive. This can be accomplished by affixing a patch of a material having sufficient tensile strength to the tissue, using a suitable adhesive. In one embodiment, an unadhered portion of the patch may then be easily grasped and moved or stabilized by suitable retraction means, such as a retracting instrument, or a suture that is passed through the unadhered portion of the patch, or which is permanently pre-attached to the patch. Alternatively, the patch may be completely adhered to the tissue, and a suture may then be passed through the adhered patch to provide tension without necessarily penetrating the tissue, or a retracting instrument may be applied to the adhesive or the patch. In each case, the patch can distribute the applied force over a larger surface area of the tissue than that which would be contacted directly by the retracting means, thus reducing potential tissue trauma, as might occur if a suture were passed directly through tissue and retracted. Moreover, the ability to achieve and maintain retraction of a tissue in a confined space using a means of retraction which minimizes obstruction of access ports is particularly important in minimally-invasive surgery, such as laparoscopy or other endoscopic surgery. This concept is particularly applicable to organs such as cardiac tissue, lung tissue, and GI (gastrointestinal) tissue in minimally invasive surgical procedures.

The above and other methods of the invention can be carried out in minimally invasive procedures, in which a tissue-affixing article that can be a patch, or a suture/patch combination can be passed through a small diameter needle access port and adhered to the target tissue. The suture then passes out of the body through the needle access port, and does not obstruct larger endoscopic ports through which the surgery may be performed. Alternatively, a retracting suture can be passed outwardly through tissue to the exterior of the body with a needle, allowing retraction without adding an access port for that purpose.

In another embodiment the invention involves securing an area of tissue internally of a patient with an adhesive and applying a force to the tissue via the adhesive thereby retracting the tissue in connection with a surgical procedure. Force can be applied to the tissue via the adhesive by grasping the adhesive directly, (via, for example, a tab formed from the adhesive material) or by applying a force to the adhesive indirectly by applying a force to an article adhered to or secured within the adhesive. For example, a patch can be adhered to the adhesive, a mesh can be formed within the adhesive when the adhesive is a fluid that is solidified by light or the like, etc.

In another embodiment a method is provided that involves percutaneously inserting a tissue-affixing article into a patient, adhering the affixing article to a tissue surface internally of the patient, and retracting the tissue surface via the affixing article.

Another aspect of the invention involves tissue-retracting devices and arrangements. In one embodiment, a tissue-affixing article is provided in combination with an adhesive and a suture fastenable to the article.

According to another embodiment the invention provides a percutaneously deliverable assembly including a distal portion constructed and arranged to be inserted into a patient percutaneously, and a proximal portion constructed and arranged to remain outside of a patient during a surgical procedure, the distal portion constructed and arranged to contain a tissue-affixing article.

The invention also provides a kit that includes a tissue-affixing article for application to and retraction of tissue internally of a patient, and an adhesive for bonding the tissue-affixing article to the tissue.

Also provided is a device for the percutaneous application of a tissue-affixing article to tissue. The device includes an obturator with a notch for holding the tissue-affixing article, and a needle or cannula for percutaneous access of the obturator.

In another aspect the invention provides the use of kits, devices, and systems as described above in surgical procedures. In one embodiment the devices, kits, or systems can be used in minimally invasive surgery. In another embodiment they can be used in open, internal surgery.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure.

DETAILED DESCRIPTION OF THE INVENTION

The Retractor and Associated Devices

Figure 1:
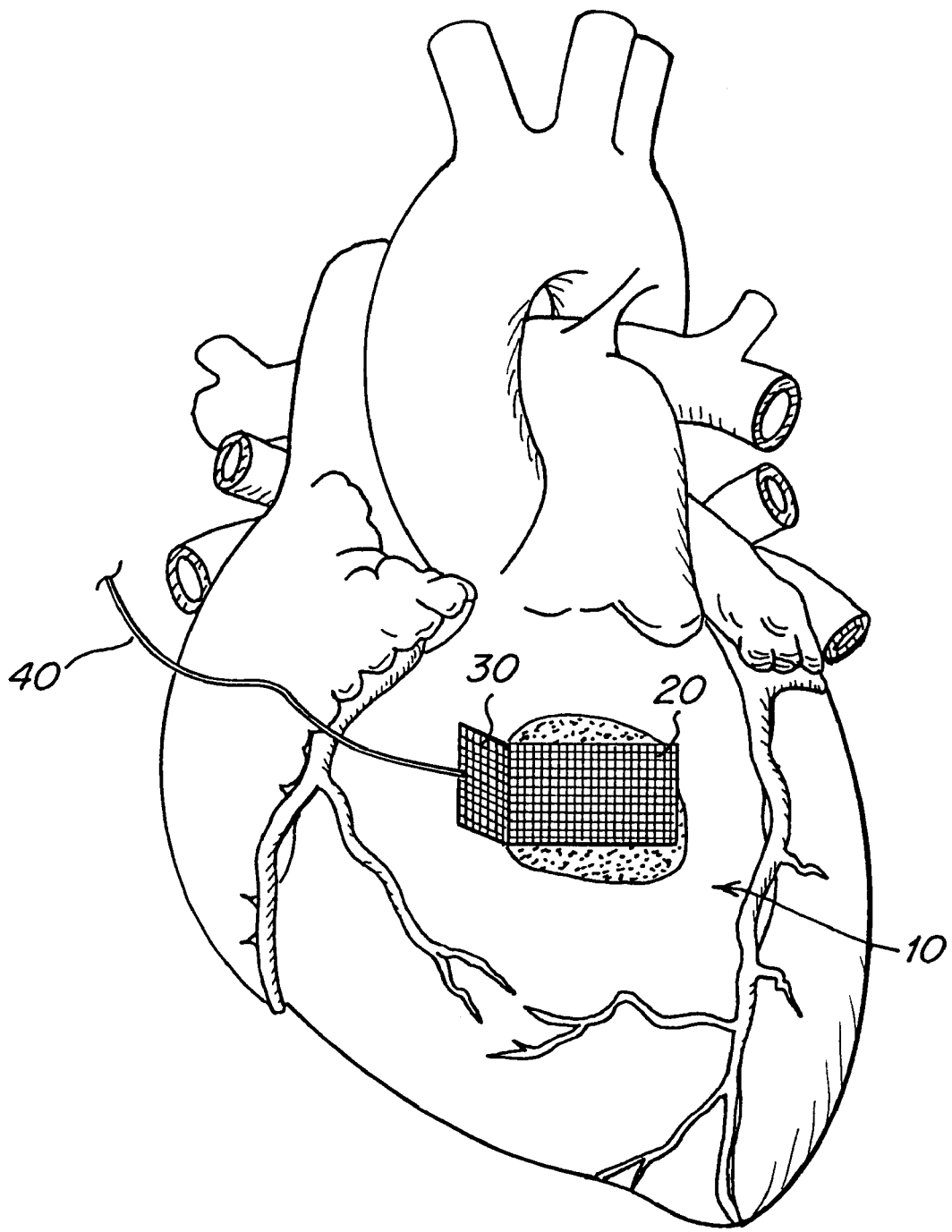
FIG. 1 illustrates schematically a tissue-affixing article connected to a suture, the tissue-affixing article adhesively secured to a tissue surface of a heart.
Figure 2:
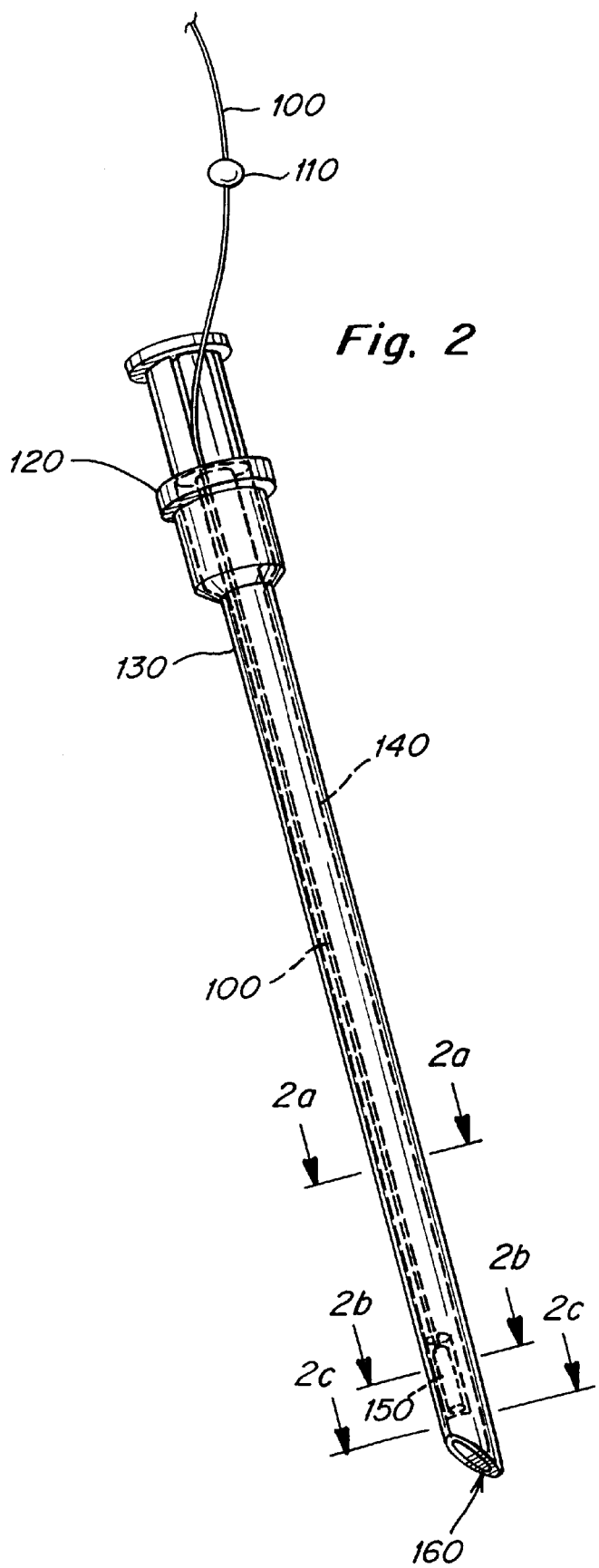
FIG. 2 illustrates, schematically, a percutaneously-insertable portal including a distal, insertable portion having a port in which is mounted a tissue-affixing article.
Figure 2A:
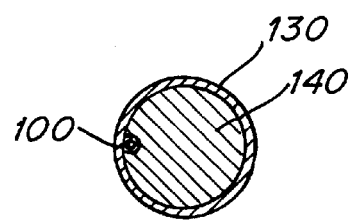
FIG. 2a is a cross-sectional view taken along line 2a—2a of FIG. 2.
Figure 2B:
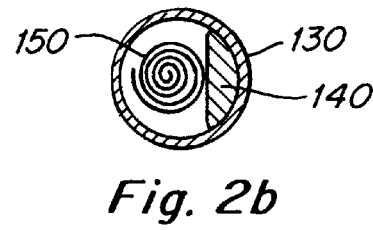
FIG. 2b is a cross-sectional view taken along line 2b—2b of FIG. 2.
Figure 2C:
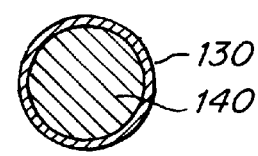
FIG. 2c is a cross-sectional view taken along line 2c—2c of FIG. 2.

FIG. 1 is a schematic illustration of a tissue-affixing article (20) which has been adhered to a surface of tissue (10) external of a heart by a biologically-compatible adhesive, and to which retractive force is being applied to an unadhered tab (30) of the patch via a suture (40). FIG. 2 shows an embodiment of a percutaneously-passable application assembly for percutaneously inserting a rolled tissue-affixing article (150) with a pre-attached suture (100) with an optional retainer (110). The rolled-up tissue-affixing article is placed in a notch in an obturator (140), as shown in cross section 2b—2b, with the suture running in a groove in the obturator as shown in cross section 2a—2a. The obturator is enclosed in a needle (130), which may be capped at the extracorporeal (proximal) end with a removable lock-out (120) to prevent motion of the obturator during insertion of the needle. The needle defines one embodiment of a "portal" as that term is used herein, the obturator and needle together defining one embodiment of a percutaneously passable assembly (160) of the invention. After insertion of the needle through the skin and into the body cavity where retraction is to occur, the obturator is advanced and the tissue-affixing article is removed from the notch in the obturator. The obturator and optionally the needle may then be removed, leaving only the suture passing through the wall of the body cavity. The tissue-affixing article is then adhered to the target tissue to allow retraction thereof.

In use, the device illustrated in FIG. 2 can be used to apply the tissue-affixing article to the tissue surface, for example via tamping or pressing the tissue-affixing article onto the surface, or another device can be used. For example, the portal can be inserted percutaneously (via a puncture created by the needle, through a trocar cannula, or the like) and another instrument, optionally inserted through another incision, can be used to manipulate the tissue-affixing article and apply the tissue-affixing article to tissue. The device illustrated in FIG. 2 can include (not shown) an adhesive-dispensing port, and an emitter of electromagnetic radiation such that, in the embodiment described in which a photo-activated adhesive is used to secure the tissue, the device in FIG. 2 can be used to deploy the tissue-affixing article, to apply adhesive to a tissue surface, and to photo-adhere the tissue to the tissue-affixing article. The tissue-affixing article can be applied entirely via the device of FIG. 2 in that embodiment. In other embodiments the tissue-affixing article will be deployed by the device of FIG. 2, another device will be used to apply a photoadhesive to the tissue surface and to apply the tissue-affixing article to the photo-adhesive and photo-adhere the tissue to the tissue-affixing article.

In a more complex arrangement, not illustrated, the device which inserts the tissue-affixing article percutaneously can also be used to deploy and adhere the tissue-affixing article. For example, the tissue-affixing article could be pretreated with dried adhesive, as described below, and could be loosely attached to a set of expandable prongs, for example of the type used for retrieving small objects in mechanical repairs. Then after percutaneous insertion, the tissue-affixing article is expanded by the prongs, applied to the tissue and allowed to hydrate in bodily fluids or supplementally added fluids to activate the adhesive. Then the adhesive is cured, either by external means, such as light or a sprayed chemical, or by self-activation from the water in the bodily and supplementally added fluids. After appropriate curing time, which can be determined in advance, the retractor is ready for use.

Materials for the Tissue-affixing article

The invention comprises, in one embodiment, at least two material components, a medically acceptable tissue-affixing article and a tissue-compatible adhesive for the tissue-affixing article. These may be combined for convenience of application. Further optional elements include retraction elements, such as a pre-attached suture or a tab for grasping or for peeling. When the retraction elements include a tab, the tab may be a separate element that is attachably connected to the tissue-affixing article, or the tab may be formed from an area of the tissue-affixing article itself that is not adhered to the tissue surface. Additional optional elements include biologically active materials. In another embodiment the invention comprises a tissue-compatible adhesive, and an adhesive-manipulating object such as a forceps or the like for physically manipulating the adhesive directly, preferably percutaneously, thereby retracting the tissue.

The tissue-affixing article material and/or adhesive, after application to tissue and curing (if required) of the adhesive, must possess sufficient mechanical strength and tenacity to withstand the force required to retract the tissue when such force is applied to tissue-affixing article material and/or adhesive at a single point, such as via a suture or a forceps. The tissue-affixing article and/or adhesive must distribute the force over a sufficient area of the tissue surface to allow retraction without damage. As used herein, "force" is meant to define the application of a physical force, as opposed to a driving force in chemical equilibria, osmotic pressure, or the like. A "force", in the context of the invention, if left unopposed, causes physical movement of the tissue.

The tissue-affixing article can be a patch made of Vicryl™ degradable mesh or of Mersilene™ non-degradable mesh which is believed to have sufficient strength for the purposes of the invention. The patch material may be the adhesive material, if the adhesive has sufficient tensile strength once cured.

Alternatively, the tissue-affixing article can be a portion of adhesive itself,

The tissue-affixing article, or patch, may be formed of any of a variety of materials, in any suitable form, which are suitable for surgical use. Physical forms suitable for application include, but are not limited to, filaments, fibrils, meshes, fabrics, felts, sponges, membranes, imperforate films and wafers, and pre-formed adhesives or adhesive precursors. The physical form is most typically preformed before application to the tissue surface, but may also form spontaneously, for example as a phase-separation-created membrane or coacervate, after application. The materials used to make the tissue-affixing article or patch can include any material with adequate biocompatibility and sufficient tensile strength. Materials known to be suitable for medical use are preferred. Suitable materials include, but are not limited to, polyolefin meshes, such as Mersilene™ mesh described below; poly(fluorinated alkylene) membranes and meshes, such as Gore-Tex™ perfluoropolymers; medical-grade materials in general, including polyurethanes, polyolefins, polycarbonates, silicones, polyesters, polyacrylates and polyamides; natural fibers of cotton, silk, alginate and the like; and inorganic materials such as glass, ceramic and metal. The tissue-affixing article or patch can be an elastomer as described in U.S. Pat. No. 5,026,389, incorporated herein by reference.

Degradable materials are preferred, especially when the materials are to be left behind after the surgical procedure. Many suitable degradable materials are commercially available, such as Vicryl™ mesh; these are commonly made of the same homopolymers and copolymers used to make absorbable sutures. Monomers for such polymers include but are not limited to lactide, glycolide, caprolactone, 1,3-dioxan-2-one and other aliphatic carbonates, 1,4-dioxan-2-one, anhydrides, and orthocarbonates. Polymers of absorbable natural materials such as proteins and polysaccharides are also useful, if formed so as to have suitable tensile properties. Such materials include catgut and other collagenous materials, and degradable saccharides such as hyaluronic acid, alginate or partially oxidized cellulose.

Degradable materials will be preferred for many purposes. The exact degradation time is not, in most cases, an important variable as long as it is sufficiently long to allow completion of the operation. When used solely for retraction, the tissue-affixing article or patch material is preferably biodegradable, so that it may be left in place after the operation. Non-degradable materials are preferred if the tissue-affixing article or patch is intended to also serve an ancillary function, such as reinforcement of the tissue location. Degradable mesh materials are particularly preferred.

The Adhesive Component

The adhesive may be any medically acceptable adhesive which provides a sufficiently strong bond between the tissue-affixing article or patch and the tissue to withstand the forces involved in retraction of the tissue. Examples of suitable adhesives include those disclosed in U.S. Pat. No. 5,026,389, referenced above, or as described in U.S. Pat. No. 4,621,619, incorporated herein by reference. The adhesive should be strong enough and bond sufficiently well so that, when a 1 $cm^2$ tissue-affixing article or patch is adhered, via the adhesive, to an organ weighing about 200 g, (such as, depending on species, a heart, liver, or spleen,) the organ can be easily moved, or prevented from moving (stabilized), for example rotated, elevated, and the like via force applied to the organ via the adhesive. The adhesive bond typically will have a strength of at least 1000 g in a 90 degree peel test, preferably at least 1500 g, more preferably still at least 2000 g in this test. As used herein, all physical manipulations of tissue of this nature (rotation, elevation, translation, transposition, and the like, or prevention thereof) will be called "retraction", which is to be understood to apply to any method of physical manipulation or physical stabilization of interior organs, structures, and tissues of the body entailing movement or prevention of movement thereof.

Some preferred adhesives will be formed in situ by reaction of active monomers. Frequently, these reactive monomers will be based on macromolecules, both for mechanical stability and to minimize toxicity. These larger monomers are also known as "macromers". However, in the discussion herein, the terms "macromer" and "monomer" are not distinguished from each other unless specifically so stated.

One set of suitable adhesives are disclosed in detail in International Patent Publication No. WO 96/29370 and in co-pending, commonly-owned U.S. patent application Ser. Nos. 08/478,104 and 08/710,689, which are hereby incorporated by reference. These documents disclose adhesive gel materials which adhere strongly to tissue, yet are biodegradable. The synthesis of such polymers is described in U.S. Pat. No. 5,410,016, incorporated herein by reference, in which application of biodegradable macromers to tissue, followed by photopolymerization to form a gel, is described; while methods for forming gels on tissue surfaces are described in U.S. Pat. No. 5,573,934, incorporated herein by reference. These methods and materials, described in more detail below, are currently preferred for the invention, but other bioadhesive materials are known in the art may be suitable. Such materials include cyanoacrylates, poly(meth) acrylates, polyurethanes, and protein-containing glues incorporating collagen and fibrin. The adhesive material may be of any sort which has appropriate tissue adherence and low toxicity, and may be a solid or a gel after being cured with gels being preferred.

The adhesive is preferably biodegradable, i.e., degradable in the body to metabolizable or excreted components, and is preferably biocompatible, i.e., minimally stimulatory of inflammation or other tissue reaction.

In addition to the photopolymerizable materials described in U.S. Pat. No. 5,410,016, systems for forming adhesives on surfaces may comprise other polymers known in the art, including the polymers described in U.S. Pat. No. 4,938,763 to Dunn, et al., U.S. Pat. Nos. 5,100,992 and 4,826,945 to Cohn et al, U.S. Pat. Nos. 4,741,872 and 5,160,745 to De Luca et al, U.S. Pat. No. 5,527,864 to Suggs et al., and U.S. Pat. No. 4,511,478 to Nowinski et al., all incorporated herein by reference. These materials, which either are able to covalently crosslink by free-radical-initiated polymerization, or can be made so by known chemical modifications such as those described in U.S. Pat. No. 5,410,016, are preferred materials of the invention. In addition, materials which cross-link by other mechanisms, or which comprise low-molecular weight reactive monomers, are also potentially suitable for the invention if they are biocompatible and non-toxic.

For some applications, particularly where retraction of heavy internal structures is not a critical function, a pre-formed adhesive layer on a tissue-affixing article or patch may be suitable. However, classical pressure-sensitive adhesives can have poor adherence when surfaces are mucoid or bloody. For critical applications, of which cardiac surgery is one example, loss of adherence of a retractor can be dangerous, and highly adherent adhesives are preferred. Such highly adherent adhesives preferably include crosslinkable groups which are capable of forming covalent bonds with other compounds while in the presence of an aqueous solution. These crosslinkable groups permit crosslinking of the monomers to form a gel or solid, either after, or independently from thermally dependent gelation or preciptation of the monomer. Chemically or ionically crosslinkable groups known in the art may be provided in the monomers. The crosslinkable groups in one preferred embodiment are polymerized using photoinitiation to generate free radicals, preferably with visible or long wavelength ultraviolet radiation. The preferred crosslinkable groups are unsaturated groups including vinyl groups, allyl groups, cinnamates, acrylates, diacrylates, oligoacrylates, methacrylates, dimethacrylates, oligo(meth)acrylates, or other biologically acceptable polymerizable groups.

Other polymerization chemistries which may be used include, for example, reaction of amines or alcohols with isocyanate or isothiocyanate, or of amines or thiols with aldehydes, epoxides, oxiranes, or cyclic imines; where either the amine or thiol, or the other reactant, or both, may be covalently attached to a monomer. Mixtures of covalent polymerization systems are also contemplated. Sulfonic acid or carboxylic acid groups may be used.

Preferably, especially if the adhesive is to form a hydrogel, at least a portion of the reactive monomers will be crosslinkers, i.e., will have more than one reactive group, to permit formation of an adherent layer and/or a coherent hydrogel by ensuring the crosslinking of the polymerized monomers. Up to 100% of the monomers may have more than one reactive group. Typically, in a synthesis, the percentage will be of the order of 50 to 95%, for example, 60 to 80%. The percentage may be reduced by addition of co-monomers containing only one active group. A lower limit for crosslinker concentration will depend on the properties of the particular monomer and the total monomer concentration, but typically will be at least about 3% of the total molar concentration of reactive groups. More preferably, the crosslinker concentration will be at least 10%, with higher concentrations, such as 30% to 90%, being optimal for maximum retardation of diffusion of many drugs. Optionally, at least part of the crosslinking function may be provided by a low-molecular weight crosslinker. When the drug to be delivered is a macromolecule, higher ranges of polyvalent monomers (i.e., having more than one reactive group) are preferred. If the gel is to be biodegradable, as is preferred in most applications, then the crosslinking reactive groups should be separated from each other by biodegradable links. Any linkage known to be biodegradable under in vivo conditions may be suitable, such as a degradable polymer block. The use of ethylenically unsaturated groups, crosslinked by free radical polymerization with chemical and/or photoactive initiators, is preferred as the crosslinkable group. The monomer may also include an ionically charged moiety covalently attached to a monomer, which optionally permits gelation or ionic crosslinking of the monomer.

Methods of Application

In a preferred embodiment, a tissue-affixing article or patch is adhered to the tissue by a process called "priming", which is described in greater detail in International Patent Publication No. WO 96/29370 and in co-pending U.S. patent application Ser. Nos. 08/478,104 and 08/710,689, now U.S. Pat. Nos. 5,844,016 and 5,900,245, respectively.

As described therein, one or more initiators are applied to a surface to form an absorbed layer. "Absorbed" is used herein to encompass both "absorbed" and "adsorbed". A solution of polymerizable molecules, referred to herein as "monomers", is then applied. There are several embodiments of this application method.

In its simplest embodiment, one or more initiators or components of an initiation system are applied directly to the surface, and the unabsorbed excess is optionally removed by washing or blotting. The initiator solution may further contain one or more polymerizable monomers, and other useful formulating ingredients, including accelerators, co-initiators, sensitizers, and co-monomers. Then a liquid, containing polymerizable monomers in combination with one or more initiators or components of an initiation system (which may be the same as or different from that absorbed in the first step) is applied. The system, if not self-polymerizing, is then stimulated to polymerize, for example by exposure to an appropriate wavelength of light.

The priming and monomer-application steps can also be combined. For example, if excess initiator is not removed before monomer addition, then subsequent application of monomer will result in mixing of initiator into the monomer layer. Similarly, if the monomer layer contains an initiator with a high affinity for the surface, then it is possible to apply a monomer layer containing initiator, and wait an appropriate time to allow preferential absorption of the initiator to the surface to achieve the same effect.

All of these methods may collectively be described as application of the monomer in an "initiator-incorporating manner", encompassing any means of application and mixing which results in both an absorbed layer of initiator, and a layer of monomer incorporating an initiator, being present on a surface to be coated.

The initiators may be chemical, photochemical, or a combination thereof. With non-photochemical systems, a reductant component and an oxidant component may be present in the two parts of the solution, i.e., in the priming layer and the coating layer.

Alternatively, a two-step process can be used to form polymers, especially bioabsorbable hydrogels, on tissue. In the first step, the tissue is treated with an initiator or a part of an initiator system for the polymerization of olefinic (e.g. acrylic) or other functional monomers, optionally with monomer in the priming solution. This provides an activated tissue surface. In the second step, monomer(s) and, if appropriate, the remainder of an initiator system, are together placed in contact with the activated tissue, resulting in polymerization on the tissue. An example of such a system is the combination of a peroxygen compound in one part, and a reactive ion, such as a transition metal, in another.

This process of spontaneous polymerization does not require the use of a separate energy source. Moreover, since the process of polymerization is initiated when part one contacts part two, there are no "pot life" issues due to initiation of polymerization. If desired, part one or part two can contain dyes or other means for visualizing the hydrogel coating.

In application of a photoiniated process to adhere a patch to tissue, the tissue, and preferably the patch as well, are stained (primed) with a photoinitiator, optionally also containing a polymerizable material, and then a polymer solution having added thereto a defined amount of the same or a different photoinitator is applied to the tissue and to the patch. The patch is applied to the tissue region either before or after application of the primer and the polymer solution. On exposure to light, the resulting system polymerizes to form a gel throughout the applied volume which has excellent adherence both to the tissue and to the patch. As used herein, "photoadhere" is meant to define adhering an article to a tissue surface using electromagnetic radiation, as described for example in the discussion above.

Thus, a tissue-affixing article or patch may be applied onto the adhesive, or can be a mesh or other arrangement that can be contained within a fluid pre-adhesive which is hardened and adhered to tissue and encases the tissue-affixing article or patch. A tab, suture, or other component affixed to the tissue-affixing article or patch may be allowed to extend outside of the hardened adhesive to be grasped by the operator, optionally via an instrument, for manipulation of tissue via the adhesive.

In any adhesive system, especially in one involving more than one component, one or more of the components of the adhesive system may be applied to the tissue-affixing article or patch before its application to tissue. For example, some or all of the components of an adhesive system could be dried or lyophilized onto the tissue-affixing article or patch. On application to tissue, fluid would be absorbed, reconstituting the adhesive. The adhesive could then polymerize or otherwise adhere to the tissue, via an external stimulus such as light or via endogenous chemical reactions.

In a further embodiment, the degree of adhesion of the tissue-affixing article or patch to the tissue, which is provided by the adhesive, can be tailored, for example to resist the stress of retraction, but to allow removal by peeling from an edge, or by other atraumatic removal procedures. If edge-peeling for removal is contemplated, the retraction point (suture, tab, or point of application of forceps to the adhesive surface) is preferably near the middle of the tissue-affixing article or patch or adhesive area; and retraction force should be applied substantially normal to the plane of the tissue-affixing article or patch.

In a further embodiment, an anchoring patch could be provided within the body cavity, allowing the retracted organ or tissue to be secured, via an attached patch, to the anchoring patch, for example via a suture, staple or clip. Alternatively, the surfaces of a retracting patch and an anchoring patch could interact, as in Velcro™ loop/hook closures.

Biologically Active Agents

In any embodiment, the applied tissue-affixing article or patch, the adhesive, or both can contain biologically active ingredients such as drugs for local or systemic controlled release. The active materials can provide therapy for existing conditions, or for the effects of the surgery itself, or as ancillaries to a medical treatment (for example, antibiotics) or as the primary objective of a treatment (for example, a gene to be locally delivered). A variety of biologically active materials may be included, including passively-functioning materials such as hyaluronic acid, as well as active agents such as growth hormones. All of the common chemical classes of such agents are included: proteins (including enzymes, growth factors, hormones and antibodies), peptides, organic synthetic molecules, inorganic compounds, natural extracts, nucleic acids, lipids and steroids, carbohydrates, glycoproteins, and combinations thereof. Further examples include analgesics (for example, Lidocaine™), anti-irritants, anti-inflammatory agents (both steroidal and nonsteroidal), regulators of wound healing, growth factors and antagonists, and hemostatic agents.

Examples for use in particular applications include antithrombotic agents (e.g., prostacyclin and salicylates), thrombolytic agents (e.g. streptokinase, urokinase, tissue plasminogen activator (TPA) and anisoylated plasminogen-streptokinase activator complex (APSAC)), vasodilating agents (e.g. nitrates, calcium channel blocking drugs), anti-proliferative agents (e.g. colchicine and alkylating agents, intercalating agents), growth modulating factors (such as interleukins, transformation growth factor 8 and congeners of platelet derived growth factor, monoclonal antibodies directed against growth factors), and other agents which may modulate local or systemic physiological function, or the healing response to organ injury post intervention.

The adhesive material may also incorporate cells as therapeutic agents, such as cells producing drugs (including growth factors and inhibitors), or progenitor cells, for example progenitors of the same cell type as the involved organ, to accelerate healing processes.

Sites of Retraction

The invention is applicable to retraction of any organ or internal tissue. In addition, the techniques and devices of the invention can also be used for the retraction of external tissue, such as skin. The retraction method is especially critical with "soft" organs, for which, to the knowledge of the inventors, there are no truly satisfactory non-damaging methods of retraction at present. These include, without limitation, liver, spleen, pancreas, gall bladder, and kidney; components of the gastrointestinal tract, including stomach and intestine; components of the genitourinary tract, including bladder, uterus, ovary, fallopian tubes, and testicles; compression-sensitive organs such as nerve bundles, spinal cord and brain; the lungs; and the eye and internal components thereof.

The invention is also useful for retraction or displacement of more muscular tissues, where conventional retraction can leave bruises. As shown in the example below, the compositions and methods of the invention can be applied to the beating heart. Other muscular tissues which could be manipulated include the tongue, the uterus, and major blood vessels including the aorta and vena cava. The invention could also be used for positioning a tissue wall, such as a chest wall or the abdominal wall, during laparoscopic and similar procedures. While such structures can be manipulated with current devices, the required devices can be bulky and obstructive compared to the invention.

The size of the applied tissue-affixing article or patch will be scaled to the size of the target organ or area. For example, a larger adhered area will be preferred for a liver compared to a spleen. Alternatively, the adhesive strength of the adhesive bond to the tissue can be varied by manipulation of the adhesive or of the application technique. For small components, for example in the eye, inner ear or ovary, the required area of adhesive will be small, and it may be sufficient to adhere a knotted or looped suture as the retracting component, or to apply force to the adhesive directly without reinforcement. There is no sharp lower limit to the size of the applied adhesive area which might be useful in microsurgery. On the other hand, for retraction of the abdominal wall, for example in minimally-invasive surgery, a relatively large area of the skin could be adhered with reinforced adhesive, to spread the retraction force widely over the relatively friable epidermis.

EXAMPLE

The nature of the invention is clearly demonstrated by an operational example. The technique was used to manipulate the beating heart of a live dog. A primer solution buffered to physiological pH and containing 50 ppm Eosin Y, 0.10 M neutral triethanolamine (TEA) buffer, and 10% of a polymerizable macromer (which contained a polyethylene glycol backbone (3500 MW) with about 5 lactate residues attached, and endcapped with acrylic acid esters) was brushed onto a tissue-affixing article, specifically a 2 cm by 4 cm area of a 2 cm×6 cm polyester (Mersilene™) mesh patch, and also onto the epicardial surface of the LV apex of a beating dog heart that was exposed via thoracotomy. A layer of sealant prepolymer (20% 35,000 MW PEG with trimethylene carbonate linkages and acrylate end caps) also containing Eosin Y and TEA buffer were applied over the primer on the heart. The mesh was placed onto the coated tissue, and a layer of sealant was brushed onto the mesh/tissue surface. Two 20-sec pulses of visible light (approx. 500 mW) were applied to the laminate to crosslink it, thereby forming a layer of hydrogel on the surface of the tissue in which the mesh was embedded. The gel, as expected, was strongly adherent to both the tissue surface and to the mesh.

The free portion of the mesh (2×2 cm) was then gripped with a conventional mechanical retractor, and used to lift the beating heart out of the opened pericardium, pointing the apex upward. The retractor was then released, and a suture was passed through the gel/mesh composite (but not the tissue) and likewise used to retract the heart. The heart continued to beat normally throughout the application and retraction.

The adhesive gel used to adhere the mesh to the heart surface was a material designed as a tissue sealant and disclosed in more detail in International Patent Publication No. WO 96/29370 and in co-pending U.S. patent application Ser. Nos. 08/478,104 and 08/710,689, now U.S. Pat. No. 5,844,016 and 5,900,245, respectively. The prepolymers were synthesized according to U.S. Pat. No. 5,410,016.

The ability to manipulate a beating heart during surgery without trauma to the heart muscle is important in virtually all cardiac surgery, especially in minimally-invasive surgery, and in particular in cardiac bypass operations. Arteries requiring replacement may be located on the posterior ("back") side of the heart, requiring sustained retraction for access to these areas.

What is claimed is:

1. A method comprising:

applying an adhesive to an area of tissue internally of a patient;

photoadhering the adhesive to the area of tissue by photopolymerizing the adhesive while in contact with the tissue;

and applying a force to the tissue via the adhesive thereby retracting the tissue during a surgical procedure.

2. A method as in claim 1, comprising percutaneously applying the force to the tissue.

3. A method as in claim 1, comprising applying the force to the tissue through a portal that passes percutaneously into the patient.

4. A method as in claim 3, wherein the portal is a needle.

5. A method as in claim 3, wherein the portal is a trocar cannula.

6. A method as in claim 1, comprising first applying the adhesive to the area of tissue; securing the tissue via the adhesive by adhering a patch to the adhesive; and then retracting the tissue by applying a force to the patch.

7. A method as in claim 6, comprising applying the adhesive to the tissue; applying the patch to the adhesive; and then photoadhering the adhesive to the tissue.

8. A method as in claim 6, comprising applying an adhesive to the patch prior to applying the patch to the area of tissue, and then photoadhering the patch to the area of tissue.

9. A method as in claim 6, comprising priming the area of tissue and photoadhering the patch to the area of tissue.

10. The method of claim 6, wherein the patch is biodegradable.

11. The method of claim 6, wherein the patch is a filament, fabric, film, fleece, mesh, gauze, or membrane.

12. The method of claim 1, wherein the adhesive is biodegradable.

13. The method of claim 1, wherein the adhesive is made from a polymer including chemically reactive groups, and wherein said polymer is crosslinked in situ on the tissue to be adherent to the tissue.

14. The method of claim 13 wherein the polymer includes photochemically polymerizable groups.

15. The method of claim 14 wherein the polymerizable groups are unsaturated groups.

16. The method of claim 15 wherein the unsaturated groups are selected from the group consisting of acrylates, methacrylates, diacrylates, dimethacrylates, oligoacrylates, oligomethacrylates, cinnamates, vinyl groups, and allyl groups.

* * * * *